United States Patent [19]

Huibers et al.

[11] 4,446,070
[45] May 1, 1984

[54] CATALYTIC OXIDATION OF POLYNUCLEAR AROMATIC HYDROCARBONS

[75] Inventors: Derk T. A. Huibers, Pennington; Cheng-Yih Jenq, Princeton, both of N.J.

[73] Assignee: HRI, Inc., Gibbsboro, N.J.

[21] Appl. No.: 272,414

[22] Filed: Jun. 10, 1981

[51] Int. Cl.³ .................. C07C 50/18; C07C 3/00
[52] U.S. Cl. ......................... 260/369; 260/687 R; 502/170; 502/201
[58] Field of Search .............. 260/351, 365, 369, 385, 260/396 R, 396 N, 687; 568/309, 326, 323; 502/170, 201

[56] References Cited

U.S. PATENT DOCUMENTS

| | | | |
|---|---|---|---|
| 757,136 | 4/1904 | Moest | 260/385 |
| 1,103,383 | 7/1914 | Singh et al. | 260/385 |
| 3,163,657 | 12/1964 | Morgan et al. | 260/365 |
| 3,678,081 | 7/1972 | Crivello | 260/396 R |
| 3,873,580 | 3/1975 | Rennie | 568/309 |
| 4,234,749 | 11/1980 | Daly | 585/319 |

Primary Examiner—Natalie Trousof
Assistant Examiner—Raymond Covington
Attorney, Agent, or Firm—Vincent A. Mallare

[57] ABSTRACT

A process for the catalytic oxidation of polynuclear aromatic hydrocarbons in general and anthracene in particular in an oxygen-containing gas in the presence of a ceric ammonium nitrate catalyst system wherein turnover ratios are increased by: (1) use of acetic acid as solvent; (2) use of pure molecular oxygen as the oxygen-containing gas; (3) use of ammonium vanadate as a promoter; and (4) addition of acetic anhydride to react with water produced as a by-product of the oxidation reaction. By use of the filtrate, remaining after removal of anthraquinone by filtration, to catalyze the oxidation of fresh anthracene, and by addition of nitric acid to restore catalytic activity after a series of oxidation reactions, anthraquinone is produced from anthracene in a continuous system.

6 Claims, 3 Drawing Figures

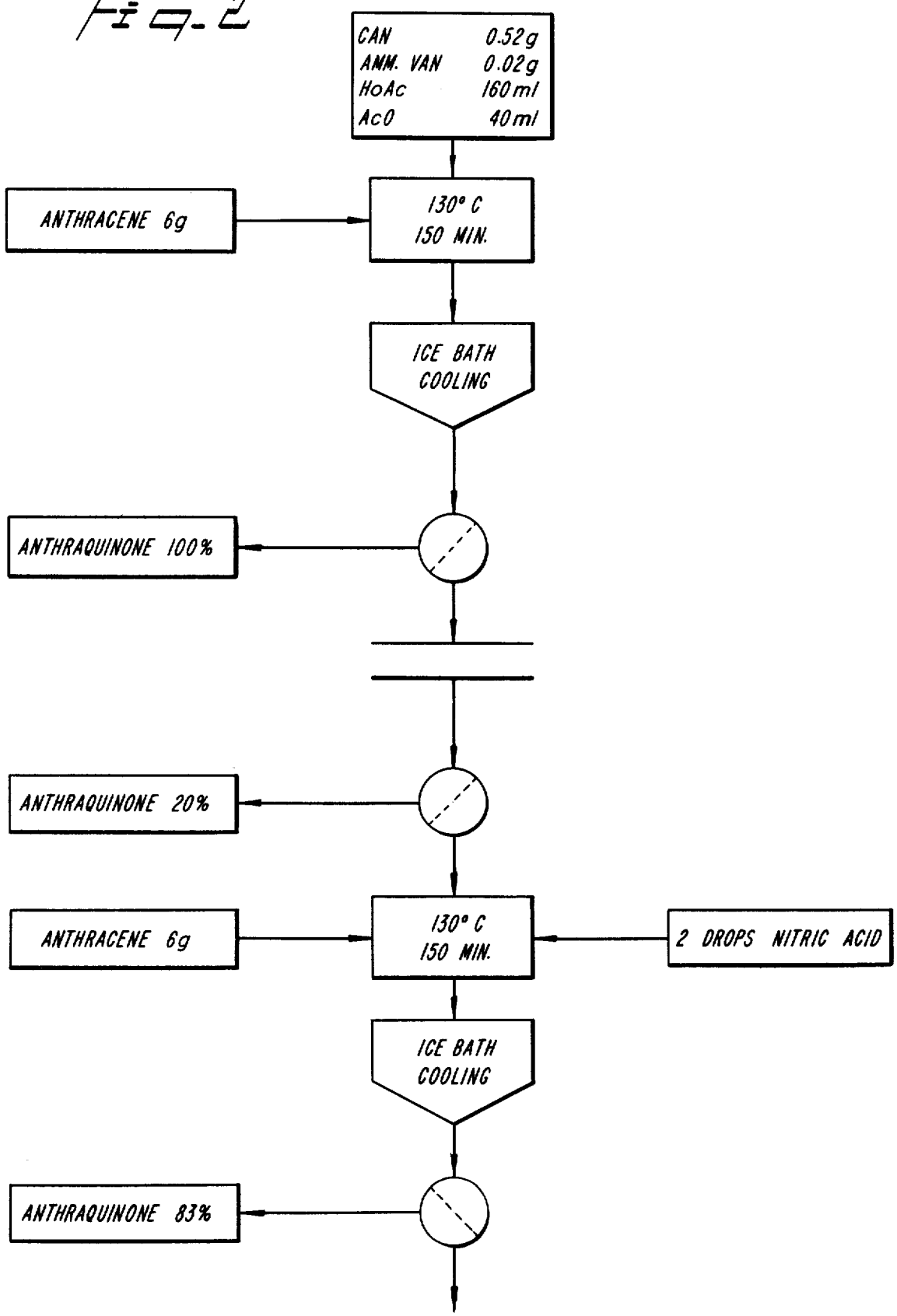

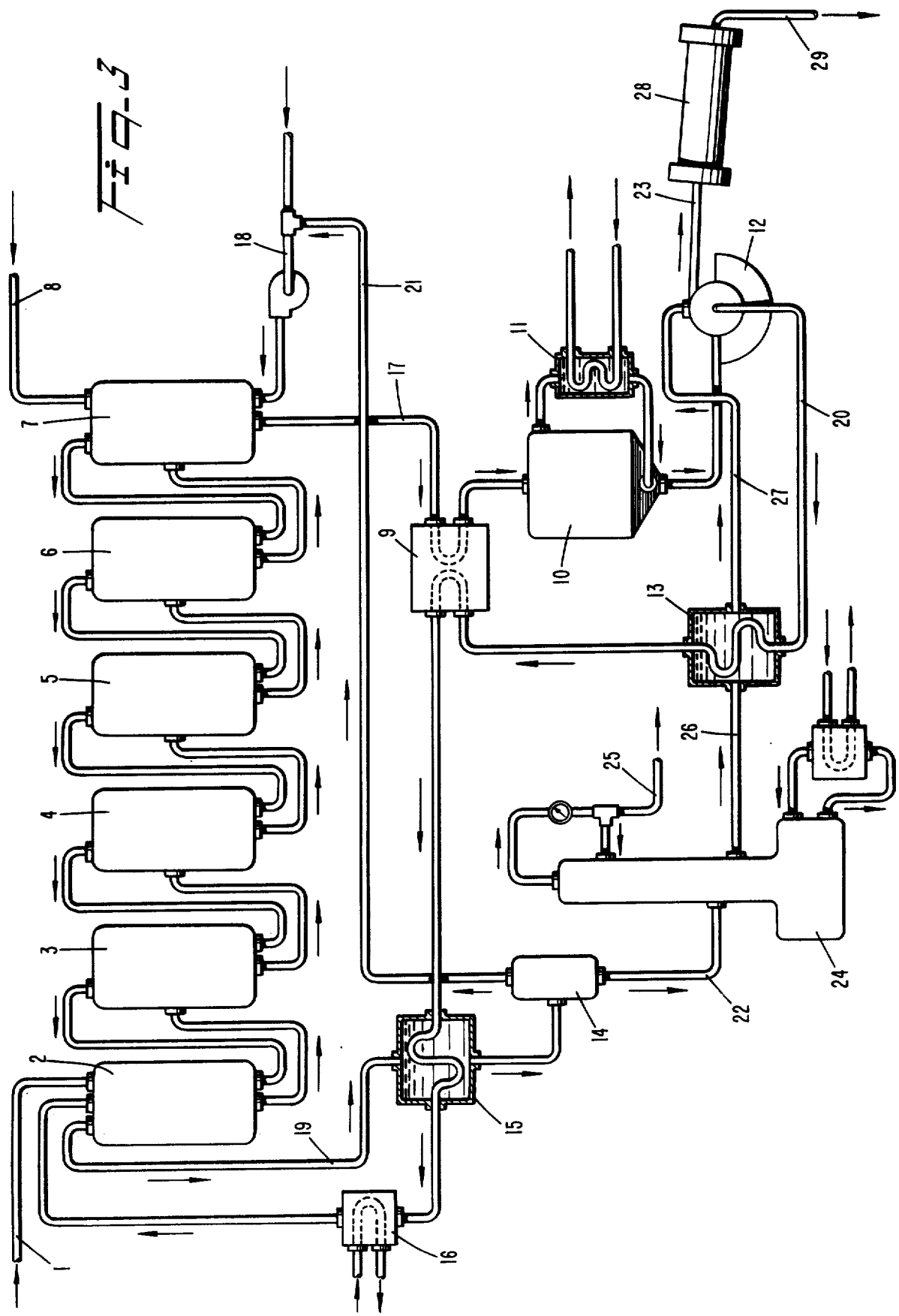

CATALYTIC OXIDATION OF POLYNUCLEAR AROMATIC HYDROCARBONS

BACKGROUND OF THE INVENTION

The present invention relates to a process for the catalytic oxidation of polynuclear aromatic hydrocarbons in general and athracene in particular.

The catalytic oxidation of anthracene is used to prepare anthraquinone. Anthraquinone is a valuable intermediate in the preparation of stable dyes for the dye industry. It has also been suggested for use as a pulping accelerator in the paper industry.

Catalytic oxidation has also been suggested as a step in the process of upgrading a mixture of polynuclear aromatic hydrocarbons. In order to upgrade polynuclear aromatic hydrocarbons, such anthracene, to more desirable mononuclear aromatic hydrocarbons, such as benzene, it has been suggested that the polynuclear aromatic hydrocarbons' reactive center rings be first weakened, and then cracked. Catalytic oxidation of the polynuclear aromatic hydrocarbons is one possible way to weaken the polynuclear aromatic hydrocarbons' center rings prior to cracking.

The catalytic oxidation of polynuclear aromatic hydrocarbons in general and anthracene in particular is taught by Daly in U.S. Pat. No. 4,234,749. Daly discloses both the preparation of anthraquinone by the catalytic oxidation of polynuclear aromatic hydrocarbons as a first step in a process for upgrading a mixture of polynuclear aromatic hydrocarbons to benzene. In Daly's process, the oxidizing agent is an oxygen-containing gas, and the catalyst is, inter alia, a ceric ammonium nitrate catalyst system including a potassium chlorate promoter. The oxidation proceeds at an elevated temperature of from about 65° to about 205° C. (149°–401° F.), and in the absence of water. Under these conditions, Daly reports that the turnover ratio, i.e., the number of moles of anthracene converted per mole of catalyst used, is increased several times over that used in prior art catalytic processes for converting anthracene to anthraquinone. (The entire disclosure of U.S. Pat. No. 4,234,749 is hereby incorporated by reference.)

While Daly discloses examples wherein a turnover ratio as high as 1.30 was achieved, further increase inthe turnover ratio is desirable. By increasing the turnover ratio the amount of catalyst consumed by the oxidation reaction can be reduced, thereby decreasing production costs of the overall processes.

SUMMARY OF THE INVENTION

It is, therefore, a main object of the present invention to improve processes for the catalytic oxidation of polynuclear aromatic hydrocarbons in general and anthracene in particular by overcoming the above-mentioned drawbacks.

It is a more specific object of the present invention to provide a process for the catalytic oxidation of polynuclear aromatic hydrocarbons in general and anthracene in particular in the presence of a ceric ammonium nitrate catalyst system which achieves a higher turnover ratio than prior art processes for doing the same, thereby reducing the amount of catalyst consumed by the oxidation reaction, and thus, decreasing the production costs of processes which utilize this reaction.

A still further object of this invention is to provide a catalyst system for the oxidation of polynuclear aromatic hydrocarbons in an oxygen-containing gas which is superior to prior art catalyst systems for doing the same, and which can be used either to prepare anthraquinone from anthracene, or to oxidize the center rings of polynuclear aromatic hydrocarbons as part of a process for upgrading the polynuclear aromatic hydrocarbons to mononuclear aromatic hydrocarbons.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the invention comprises a process for the preparation of anthraquinone from anthracene by the oxidation of anthracene in an oxygen-containing gas in the presence of ceric ammonium nitrate catalyst system wherein acetic acid is used as a solvent.

To further achieve the objects and in accordance with the purpose of the invention, as embodied and broadly described herein, the invention comprises a process for the preparation of anthraquinonone from anthracene by the oxidation of anthracene in an oxygen-containing gas in the presence of a ceric ammonium nitrate catalyst system wherein said oxygen-containing gas is pure oxygen.

To further achieve the objects and in accordance with the purpose of the invention, as embodied and broadly described herein, the invention comprises a process for the preparation of anthraquinone from anthracene by the oxidation of anthracene in an oxygen-containing gas in the presence of a ceric ammonium nitrate catalyst system wherein the ceric ammonium nitrate catalyst system includes ammonium vanadate.

To further achieve the objects and in accordance with the purpose of the invention, as embodied and broadly described herein, the invention comprises a process for the preparation of anthraquinone from anthracene by the oxidation of anthracene in an oxygen-containing gas in the presence of a ceric ammonium nitrate catalyst system wherein acetic anhydride is used to react with water formed as a by-product of the oxidation reaction.

To further achieve the objects and in accordance with the purpose of the invention, as embodied and broadly described herein, the invention comprises a continuous process for the preparation of anthraquinone from anthracene which includes the steps of oxidizing anthracene to anthraquinone in an oxygen-containing gas in the presence of a ceric ammonium nitrate catalyst system, removing the anthraquinone from the oxidation reaction product by filtration, and recycling the filtrate remaining after the removal of the anthraquinone to catalyze the oxidation of fresh anthracene.

To further achieve the objects and in accordance with the purpose of the invention, as embodied and broadly describe herein, the invention comprises a continuous process for the preparation of anthraquinone from anthracene which includes the steps of oxidizing anthracene to anthraquinone in an oxygen-containing gas in the presence of a ceric ammonium nitrate catalyst system, removing the anthraquinone from the oxidation reaction product by filtration, and recycling the filtrate remaining after the removal of the anthraquinone to catalyze the oxidation of fresh anthracene, and wherein nitric acid is added after one or more oxidation steps.

To further achieve the objects and in accordance with the purpose of the invention, as embodied and broadly described herein, the invention comprises a catalyst system for the oxidation of polynuclear aromatic hydrocarons in an oxygen-containing gas comprising ceric ammonium nitrate and ammonium vanadate.

To further achieve the objects and in accordance with the purpose of the invention, as embodied and broadly described herein, the invention comprises a catalyst system for the oxidation of polynuclear aromatic hydrocarbons in an oxygen-containing gas comprising ceric ammonium nitrate and nitric acid.

To further achieve the objects and in accordance with the purpose of the invention, as embodied and broadly described herein, the invention comprises a catalyst system for the oxidation of polynuclear aromatic hydrocarbons in an oxygen-containing gas comprising ceric ammonium nitrate dissolved in a solvent being acetic acid.

The foregoing and other objects, features, and advantages of the present invention will be made more apparent from the following description of the preferred embodiments. The accompanying drawings, which are incorporated in and constitute a part of this specification, illustrate several preferred embodiments of the invention, and, together with the description, serve to explain the principles of the invention.

BRIEF DESCRIPTION OF THE DRAWINGS

FIG. 2 is a flow sheet summarizing experiments which show that the catalytic activity of a spent ceric ammonium nitrate catalyst system of the present invention can be unexpectedly regenerated by the addition of nitric acid.

FIG. 3 is a flow sheet illustrating the process flow of a proposed anthraquinone-producing plant made in accordance with the present invention.

DESCRIPTION OF THE PREFERRED EMBODIMENT

Figure 1:
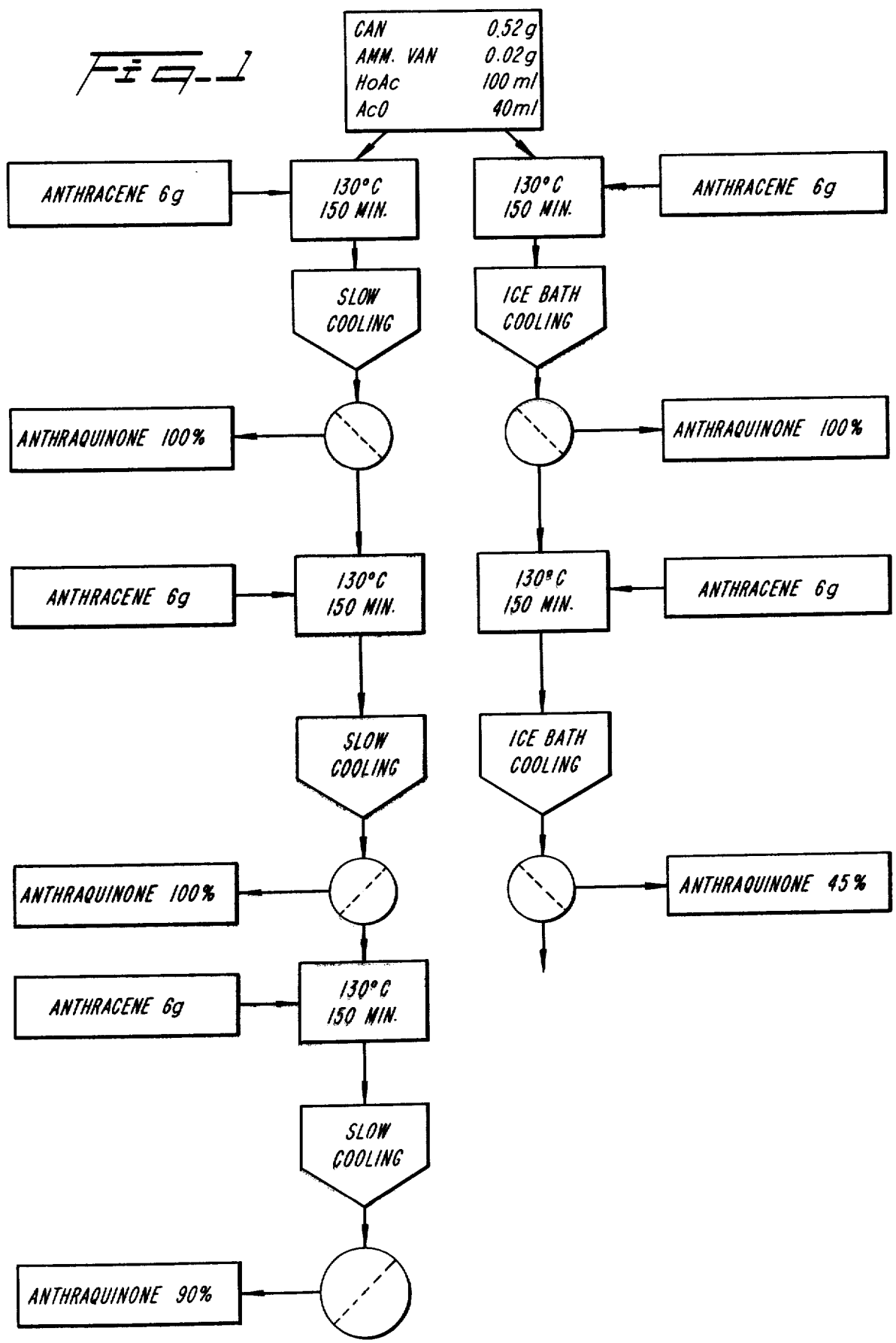
FIG. 1 is a flow sheet summarizing experiments which demonstrate that the specific ammonium nitrate catalyst system of the present invention retains considerable catalytic activity after a series of oxidation steps.

Reference will now be made in detail to the present preferred embodiments of the invention.

In accordance with the invention, polynuclear aromatic hydrocarbons in general and anthracene in particular are oxidized by an oxygen-containing gas in the presence of a ceric ammonium nitrate catalyst system using acetic acid as a solvent.

In his earlier work on the catalytic oxidation of polynuclear aromatic hydrocarbons with ceric ammonium nitrate catalyst systems, Daly taught that the polynuclear aromatic hydrocarbon/catalyst mixture can be dissolved in a suitable solvent which is water-miscible for hydrocarbons. Daly listed dimethyl sulfoxide, dimethylformamide (D.M.F.), and the tetrahydrofuran as examples of such suitable solvents.

We have discovered that by using acetic acid as the solvent for the polynuclear aromatic hydrocarbon/catalyst mixture, an unexpected increase in the turnover ratio is achieved. The oxygen-containing gas used should provide a partial pressure of oxygen jof at least about 0.5 temperature, and preferably at least about 1.0 atmosphere. The partial pressure of oxygen may range from about 0.5 to about 5.0 atmosphere.

Air may be used as the oxygen-containing gas. The oxygen content in air is about 20%. In using air the partial pressure of oxygen ranges from about 15.0 psia to about 75.0 psia or from about 0.5 to about 5.0 atmospheres.

EXAMPLE 1

The following table (Table 1) shows comparative test data obtained from the catalytic oxidation of anthracene with a ceric ammonium nitrate catalyst system. In Run #1, D.M.F., a solvent selected from the list of solvents taught by Daly, was used. In Run #2, acetic acid was used. The results show a greater than sixfold increase in the turnover ratio by using acetic acid instead of the solvent suggested by Daly.

TABLE 1

|  | Run #1 | Run #2 |
| --- | --- | --- |
| Solvent (ml) | D.M.F. 30 | Acetic Acid 30 |
| Anthracene (g) | 2.68 | 2.68 |
| Ceric Ammonium Nitrate (g) | 1.01 | 1.01 |
| Others (g) | — | — |
| Oxygen Partial Pressure | 1 atm. air | 1 atm. air |
| Reaction Time (min) | 160 | 160 |
| Reaction Time (°C.) | 127 | 127 |
| Conversion (%) | 13 | 77 |
| Turnover No. | 1.06 | 6.3 |

In accordance with the invention, polynuclear aromatic hydrocarbons in general and anthracene in particular are oxidized in the presence of a ceric ammonium nitrate system by pure molecular oxygen.

In his earlier work on the catalytic oxidation of polynuclear aromatic hydrocarbons with ceric ammonium nitrate catalyst systems, Daly taught that the oxidizing agent be a molecular oxygen containing gas, e.g., oxygen or air.

We have discovered that by using pure molecular oxygen as the oxidizing agent, an unexpected increase in the turnover ration is achieved.

EXAMPLE 2

The following Table (Table 2) shows comparative test data obtained from the catalytic oxidation of anthracene with a ceric ammonium nitrate catalyst system. In Run #1, air was used as the moleculr oxygen-containing gas. In run #2, pure molecular oxygen was used as the molecular oxygen-containing gas. The results show that the turnover was approximately three and one-half times greater when pure molecular oxygen was used than when air was used.

TABLE 2

|  | Run #1 | Run #2 |
| --- | --- | --- |
| Solvent (ml) | Acetic Acid, 60 | Acetic Acid 60 |
| Anthracene (g) | 5.36 | 5.36 |
| Ceric Ammonium Nitrate (g) | 0.52 | 0.258 |
| Others (g) | Ammonium Vanadate 0.012 | Ammonium Vanadate 0.01 |
| Oxygen Partial Pressure | 1 atm. air | 1 atm. air |
| Reaction Time (min) | 90 | 90 |
| Reaction Time (°C.) | 120–130 | 120–130 |
| Conversion (%) | 33 | 56 |
| Turnover No. | 10.5 | 35.8 |

In accordance with the invention, polynuclear aromatic hydrocarbons in general and anthracene in particular are oxidized by an oxygen-containing gas in the presence of a ceric ammonium nitrate catalyst system which includes ammonium vanadate.

We have discovered that by using a ceric ammonium nitrate catalyst system which includes ammonium vanadate, an unexpected increase in the turnover ratio is achieved. It is believed that the ammonium vanadate acts as a promoter.

EXAMPLES 3

The following table (Table 3) shows comparative tests data obtained from the catalytic oxidation of anthracene with a ceric ammonium nitrate catalyst system. In Run #1, no ammonium vanadate was used. In Run #2, 0.012 grams of ammonium vanadate was used. The results show that the turnover ratio nearly doubled when ammonium vanadate was added.

TABLE 3

|  | Run #1 | Run #2 |
| --- | --- | --- |
| Solvent (ml) | Acetic Acid, 30 | Acetic Acid 60 |
| Anthracene (g) | 2.68 | 5.36 |
| Ceric Ammonium Nitrate (g) | 1.01 | 0.52 |
| Others (g) | — | Ammonium Vanadate 0.012 |
| Oxygen Partial Pressure | 1 atm. air | 1 atm. air |
| Reaction Time (min) | 160 | 90 |
| Reaction Time (°C.) | 127 | 120–130 |
| Conversion (%) | 77 | 33 |
| Turnover No. | 6.3 | 10.5 |

In accordance with the invention, polynuclear aromatic hydrocarbons in general and anthracene in particular are oxidized by an oxygen-containing gas in the presence of a ceric ammonium nitrate catalyst system using acetic anhydride to react with water formed as a by-product of the oxidation reaction.

In his earlier work on the catalytic oxidation of polynuclear aromatic hydrocarbons with ceric ammonium nitrate catalyst systems, Daly taught that the turnover ratio could be increased by carrying out the oxidation reaction in the absence of water.

We have discovered that by using acetic anhydride to react with water formed as a by-product of the oxidation reaction, an unexpected further increase in the turnover ratio is achieved.

EXAMPLE 4

Table 4 confirms Daly's teaching as to the effect of water on the oxidation reaction. In Run #1, a solvent containing water was used. In Run #2, a solvent without water was used. The results show a greater than five-fold increase in the turnover ratio where the solvent did not contain water.

TABLE 4

|  | Run #1 | Run #2 |
| --- | --- | --- |
| Solvent (ml) | Acetic Acid, 70 30H$_2$O | Acetic Acid, 90 |
| Anthracene (g) | 5.36 | 5.36 |
| Ceric Ammonium Nitrate (g) | 0.258 | 0.258 |
| Others (g) |  |  |
| Oxygen Partial Pressure | 1 atm. Oxygen | 1 atm. Oxygen |
| Reaction Time (min) | 90 | 90 |
| Reaction Time (°C.) | 100–120 | 130–140 |
| Conversion (%) | 9.6 | 51 |

TABLE 4-continued

|  | Run #1 | Run #2 |
| --- | --- | --- |
| Turnover No. | 6.1 | 32.5 |

EXAMPLE 5

Table 5 shows further comparative test data obtained from the catalytic oxidation of anthracene with a ceric ammonium nitrate catalyst system. In both Runs #1 and #2, the solvent contained no water. The solvent used in Run #1, however, contained no acetic anhydride, whereas the solvent used in Run #2 contained approximately 10% by volume acetic anhydride. The results show nearly double the turnover ratio in the run wherein acetic anhydride was employed.

TABLE 5

|  | Run #1 | Run #2 |
| --- | --- | --- |
| Solvent (ml) | Acetic Acid, 90 | Acetic Acid, 90 Acetic Anhydride, 10 |
| Anthracene (g) | 5.36 | 5.36 |
| Ceric Ammonium Nitrate (g) | 0.258 | 0.258 |
| Others (g) | Ammonium Vanadate 0.01 | Ammonium Vanadate 0.01 |
| Oxygen Partial Pressure | 1 atm. Oxygen | 1 atm. Oxygen |
| Reaction Time (min) | 90 | 90 |
| Reaction Time (°C.) | 120–130 | 120–130 |
| Conversion (%) | 56 | 97.6 |
| Turnover No. | 38.8 | 62.5 |

In accordance with the invention, satisfactory results in the oxidation of polynuclear aromatic hydrocarbons are expected with a catalyst system comprising: 0.1 to 2.0 grams of ceric ammonium nitrate per 200 ml. solvent, and up to 0.1 grams of ammonium vanadate per 200 ml. solvent; the solvent comprising from 70 to 95% by volume glacial acetic acid and from 5 to 30% by volume acetic anhydride.

As embodied herein, a preferred catalyst system for the oxidation of polynuclear aromatic hydrocarbons in general and anthracene in particular is formulated as follows:

| | |
| --- | --- |
| Catalyst Concentration = | 0.5 Ceric Ammonium nitrate in 200 ml solvent |
| Promoter Concentration = | 0.02 Ammonium Vanadate in 200 ml Solvent |
| Solvent = | 80% Glacial Acetic Acid, 20% Acetic Anhydride |
| Temperature = | 120° C. |
| Oxygen Partial Pressure = | 1 atm. |

Experiment shows that 200 ml of this catalyst system is capable of transforming 6 g anthracene completely into anthraquinone in about 150 minutes. It should be noted that this concentration of anthracene was selected because it gave a homogeneous reaction medium. It is probable that a slurry process involving larger amounts of anthracene can be operated without serious adverse effects.

Additionally, it should be noted that the reaction time for the oxidation is dependent on both the temperature and the pressure. (Holding temperature constant, reaction time is roughly inversely proportional to oxygen partial pressure.) Accordingly, the reaction time can be reduced by increasing either the temperature or the pressure or both. Thus, a wide variety of reaction times may be achieved by use of a wide variety of temperatures and pressures. Satisfactory results are expected utilizing temperatures ranging from about 65° to about 205° C. (149° to 401° F.) and pressures ranging from 0.2 to 5 atmospheres. Optimization of the temperature and pressure to achieve a desired reaction time is within the ability of one of ordinary skill in this art.

In accordance with the invention, a continuous process for the preparation of anthraquinone from anthracene includes the steps of: oxidizing anthracene to anthraquinone in an oxygen-containing gas in the presence of a ceric ammonium nitrate catalyst system; removing the anthraquinone from the oxidation reaction product by filtration; and recycling the filtrate remaining after the removal of the anthraquinone to catalyze the oxidation of fresh anthracene. In a preferred embodiment, nitric acid is added after one or more oxidation steps to restore the catalytic acitivity of the catalyst system.

We have discovered that the ceric ammonium nitrate catalyst system of this invention unexpectedly retains considerable catalytic activity after a series of oxidation steps.

In the experiment summarized in FIG. 1, the filtrate obtained after crystallization at room temperature retained about 90% of its catalytic activity after three cycles. Ice bath cooling to accelerate crystallization caused a greater depletion of catalytic activity. However, it is suspected that this decrease was due to the fact that catalyst was trapped in the wet filter cake because cooling occurred too quickly. Accordingly, in a preferred embodiment, the reaction broth from the oxidation reaction is cooled in stages.

We have also discovered that addition of nitric acid to a spent ceric ammonium nitrate catalyst system has the unexpected property of restoring the system's catalytic activity. Accordingly, ease of regeneration is an important feature of the catalyst system of the present invention.

In the experiment in FIG. 2, the conversion from anthracene to anthraquinone in the fifth cycle was only 20%. After addition of nitric acid (2drops), however, conversion in the sixth cycle was increased to 83%.

As embodied herein, FIG. 3 illustrates the process flow of a proposed anthraquinone plant in accordance with the present invention.

Anthracene and acetic acid are fed through conduit (1) into the first reactor (2). Also, pure oxygen from conduit (18) is compressed to four atmospheres and sparged into the sixth reactor (7). While reaction broth flows through reactors from the first (2) to the sixth (7), oxygen flows countercurrently from the sixth (7) to the first (2).

Into the sixth reactor (7), catalyst make-up, including ceric ammonium nitrate, ammonium vanadate and nitric acid, is added to the reaction broth through conduit (8). The addition of catalyst into the last reactor (7) of a series is meant to drive the chemical reaction from near completion to full completion. The quantity of make-up ceric ammonium nitrate is estimated to compensate for the loss of cerium in the product crystals.

The reaction broth is withdrawn from the sixth reactor (7) through conduit (17). This reaction broth, now containing anthraquinone, is passed through heat exchanger (9), cooled down to 75° C., and then discharged into crystallizer (10), in which the reaction broth is agitated and further cooled down to 10° C. A slurry of anthraquinone crystals is discharged into filter (12).

In the filter (12) solid particles are continuously collected, washed with cool acetic acid from pipeline (27), and discharged into dryer (28) to remove acetic acid from the final product (29).

The clear solution from the filter (12), now containing disolved anthraquinone and catalyst, is passed through heat exchangers (13), (9), (15), and steam heater (16) in which it is heated in stages. It is then recycled back to the first reactor (2).

Flowing out from the first reactor (2) is the spent oxygen stream with acetic acid vapor and water vapor. This oxygen, acetic acid, water vapor mixture is cooled in heat exchanger (15) and discharged into gas-liquid separator (14), where oxygen is vented as top flow and recycled back to compressor (18). A mixture of acetic acid and water, collected as liquid in the bottom flow of the separator (14), is withdrawn and fed into distillation column (24).

In the distillation column (24), water is enriched in the overhead flow and is discarded. The bottom flow, is withdrawn and passed into heat exchanger (13), cooled, and discharged into filter (12) as washing liquid.

It will be apparent to those skilled in the art that various modifications and variations of the present invention can be made. It is intended that the present invention cover the modifications and variations of this invention provided they come within the scope of the appended claims and their equivalents.

What is claimed is:

1. A continuous process for the preparation of anthraquinone from anthracene which includes the steps of:
   (a) oxidizing anthracene to anthraquinone in an oxygen-containing gas in the presence of a ceric ammonium nitrate catalyst system dissolved in an acetic acid solvent, said oxidation taking place in a series of reactors, and the reactor broth flowing from a first reactor of said series to a last reactor of said series wherein fresh ceric ammonium nitrate catalyst system is introduced;
   (b) adding nitric acid to said oxidized anthracene;
   (c) removing the anthraquinone from the oxidative reaction product by filtration; and
   (d) recycling the filtrate remaining after the removal of the anthraquinone to catalyze the oxidation of fresh anthracene.

2. The process of claim 1 wherein a spent oxygen-containing gas stream with acetic acid vapor and water vapor is withdrawn from said first vapor.

3. The process of claim 1, which utilizes a heat exchanger to transfer heat from said spent oxygen-containing gas stream with acetic acid vapor and water vapor from said first reactor to said recycling of said filtrate to said first reactor.

4. The process of claim 2 wherein oxygen is separated from said spent oxygen-containing gas stream with acetic acid vapor and water vapor, such that oxygen is recycled to oxidize additional anthracene.

5. The process of claim 2 wherein acetic acid is separated from said spent oxygen-containing gas stream with acetic acid vapor and water vapor, such as acetic acid is recyuled for use as washing liquid for said filtration.

6. The process of claim 1, wherein the oxidation reaction product is cooled in stages.

* * * * *